United States Patent
Labudde et al.

(10) Patent No.: US 12,047,417 B2
(45) Date of Patent: Jul. 23, 2024

(54) SECURE COMMUNICATION LINK BETWEEN MEDICAL APPARATUSES OF A DATA-MANAGEMENT DEVICE

(71) Applicant: Ypsomed AG, Burgdorf (CH)

(72) Inventors: Marc Labudde, Spiegel (CH); Stefan Lindegger, Huttwil (CH); Thomas Leuzinger, Münsingen (CH); Mathias Zenger, Burgdorf (CH); Adrian Wyss, Bern (CH)

(73) Assignee: Ypsomed AG, Burgdorf (CH)

(*) Notice: Subject to any disclaimer, the term of this patent is extended or adjusted under 35 U.S.C. 154(b) by 325 days.

(21) Appl. No.: 17/474,959

(22) Filed: Sep. 14, 2021

(65) Prior Publication Data
US 2022/0070221 A1 Mar. 3, 2022

Related U.S. Application Data

(63) Continuation of application No. PCT/EP2020/055604, filed on Mar. 4, 2020.

(30) Foreign Application Priority Data

Mar. 28, 2019 (EP) .................................. 19165723

(51) Int. Cl.
H04L 9/40 (2022.01)
A61M 5/142 (2006.01)

(52) U.S. Cl.
CPC ......... *H04L 63/18* (2013.01); *A61M 5/14248* (2013.01); *H04L 63/0442* (2013.01); *A61M 2205/3584* (2013.01)

(58) Field of Classification Search
CPC ..... H04L 67/12; H04L 63/18; H04L 63/0442; H04L 9/0841; H04L 9/3215;
(Continued)

(56) References Cited

U.S. PATENT DOCUMENTS 10,896,245 B2* 1/2021 Crothall ............... H04L 67/125
2014/0281547 A1 9/2014 Modzelewski et al.
(Continued)

FOREIGN PATENT DOCUMENTS

EP 2320621 A1 5/2011
EP 3051744 A1 8/2016
(Continued)

OTHER PUBLICATIONS

International Preliminary Report on Patentability received for International Application No. PCT/EP2020/055604, mailed on Sep. 28, 2021, 9 pages.
(Continued)

*Primary Examiner* — Benjamin A Kaplan
(74) *Attorney, Agent, or Firm* — Dorsey & Whitney LLP

(57) ABSTRACT

Implementations relate to a method for establishing an end-to-end encrypted data communication link between a portable medical apparatus and a data-management device. The method comprises at least the following steps: out-of-band transmission of a public key from the medical apparatus to the data-management device, wherein the transmission does not take place via Bluetooth; setting up an encrypted Bluetooth data communication link between the medical apparatus and the data-management device; transmitting a public key from the data-management device to the medical apparatus via the Bluetooth link that has been set up; calculating a combined key on the data-management device and on the medical apparatus; setting up an end-to-end encrypted link between the medical apparatus and the data-management device using the combined key, such as a symmetrical, key.

19 Claims, 7 Drawing Sheets

(58) Field of Classification Search
CPC .............. H04L 63/0492; H04L 63/061; H04L 2209/88; H04L 63/0428; H04L 2209/805; H04W 12/50; H04W 4/80; H04W 84/18; A61M 5/14248; A61M 5/1723; A61M 2230/201; A61M 2205/3584
USPC .............................................................. 726/7
See application file for complete search history.

(56) References Cited

U.S. PATENT DOCUMENTS

| | | | |
|---|---|---|---|
| 2017/0339128 A1* | 11/2017 | Lim | .................... H04L 63/0861 |
| 2018/0091932 A1* | 3/2018 | Kwon | .................... H04W 8/005 |

FOREIGN PATENT DOCUMENTS

| | | |
|---|---|---|
| EP | 3443996 A1 | 2/2019 |
| EP | 3716567 A1 | 9/2020 |
| WO | 2016092448 A1 | 6/2016 |
| WO | 2017200989 A1 | 11/2017 |
| WO | 2018160863 A1 | 9/2018 |
| WO | 2020193090 A1 | 10/2020 |

OTHER PUBLICATIONS

English translation of International Search Report issued in International Application PCT/EP2020/055604, mailed on Mar. 25, 2020, 3 pages.

European Search Report issued in European Patent Application No. 19165723.8, mailed on Jun. 28, 2019, 3 pages.

"Bluetooth Core Specification", Version 5.0, Dec. 6, 2016, Bluetooth SIG Proprietary, retrieved from https://www.bluetooth.com/specifications/archived-specifications.

Duque, "Deep Dive into Bluetooth LE Security", Internet Post, 9 pages, posted Mar. 3, 2018, medium.com, retrieved from https://medium.com/rtone-iot-secutity/deep-dive-into-bluetooth-le-secutiy-d2301d640bfc.

* cited by examiner

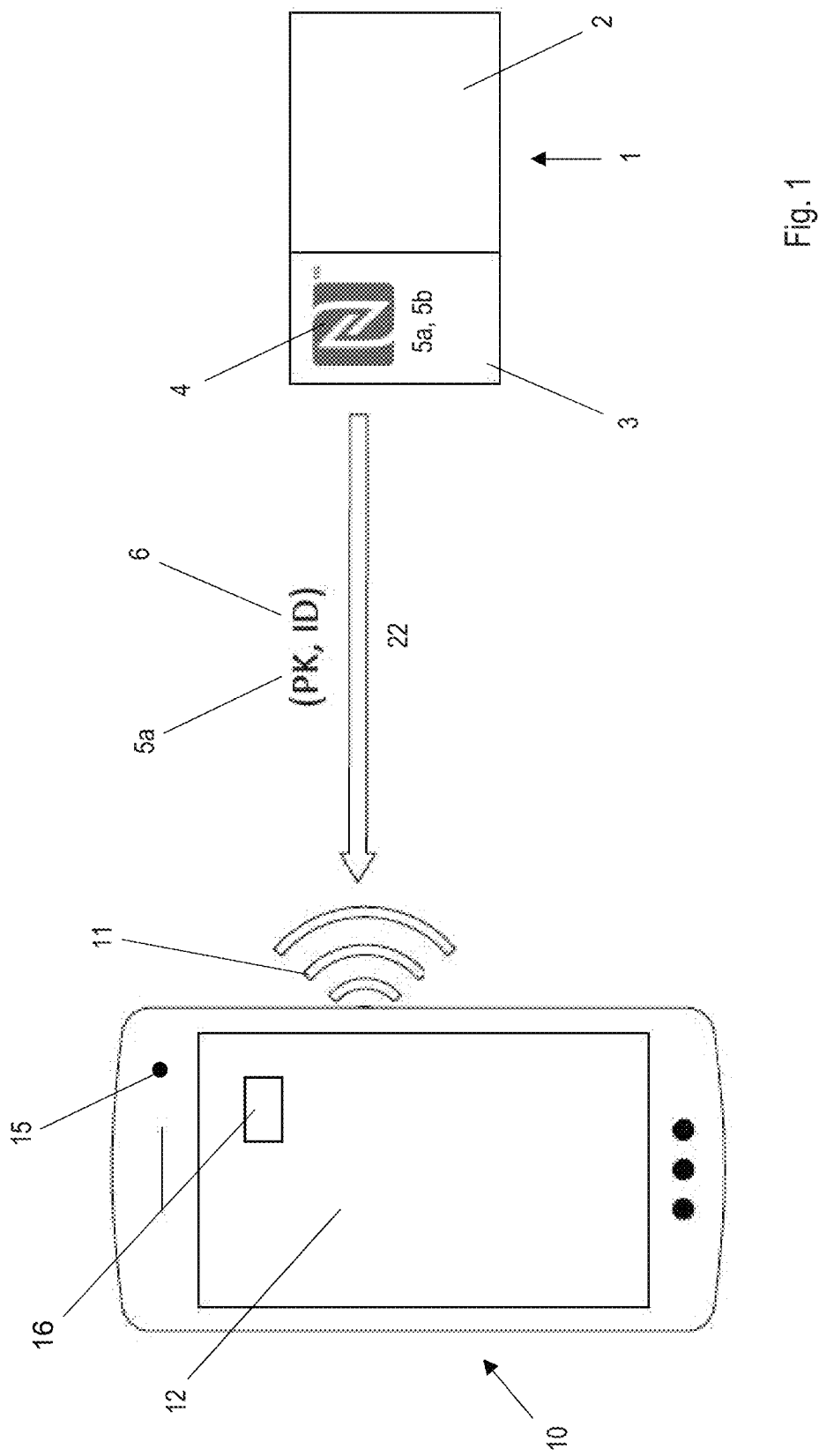

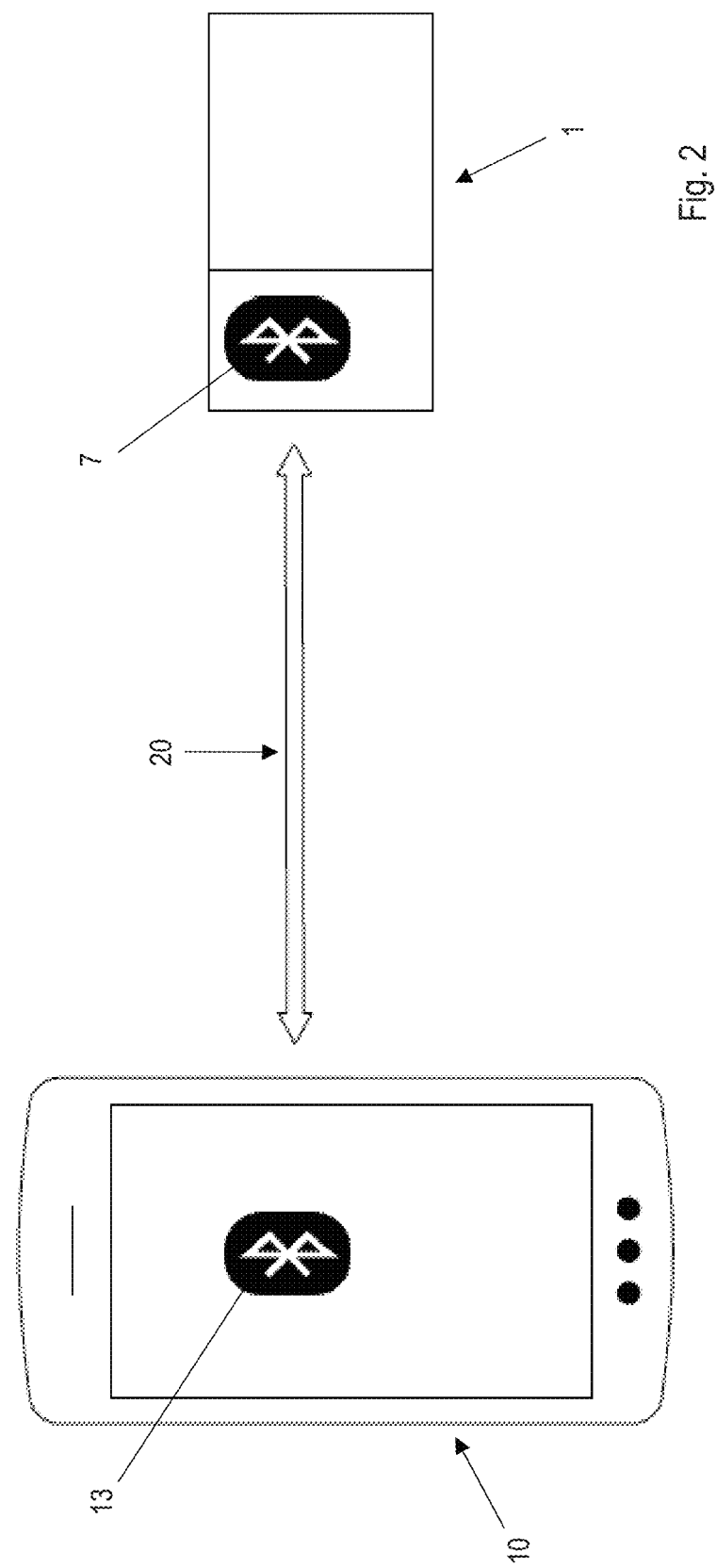

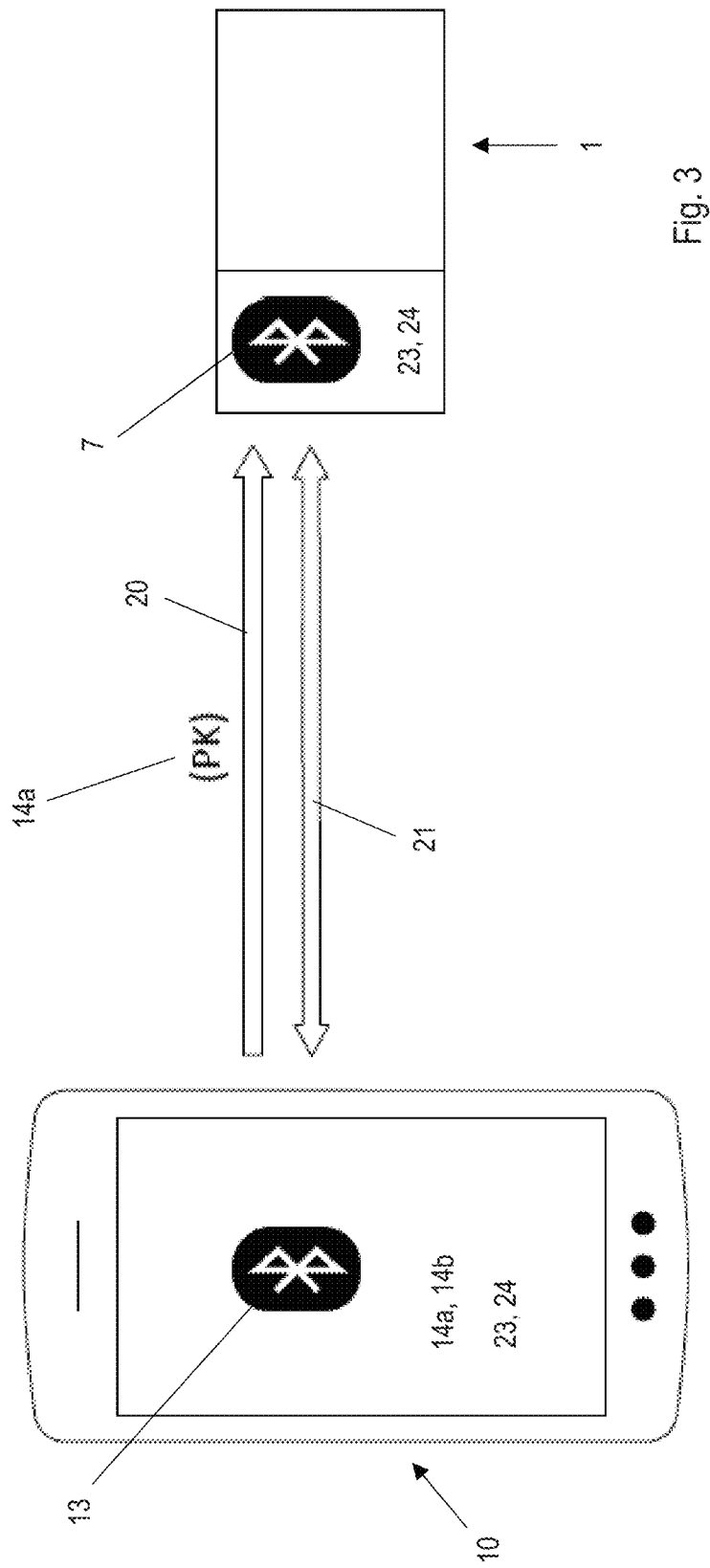

SECURE COMMUNICATION LINK BETWEEN MEDICAL APPARATUSES OF A DATA-MANAGEMENT DEVICE

CROSS REFERENCE TO RELATED APPLICATIONS

This application claims priority to International Patent Application No. PCT/EP2020/055604, filed Mar. 4, 2020, entitled "SECURE COMMUNICATION LINK BETWEEN MEDICAL APPARATUSES OF A DATA-MANAGEMENT DEVICE," which in turn claims priority to European Patent Application No. 19165723.8, filed Mar. 28, 2019, entitled "SECURE COMMUNICATION LINK BETWEEN MEDICAL APPARATUSES OF A DATA-MANAGEMENT DEVICE", each of which is incorporated by reference herein, in the entirety and for all purposes.

TECHNICAL FIELD

The present disclosure relates to the field of self-therapy using injection and infusion apparatuses and the associated therapy data management, in particular, the establishment of secure data transmission links between therapy-related apparatuses and data management devices.

BACKGROUND

Portable medical apparatuses such as injection apparatuses, portable infusion pumps or even blood sugar measuring devices are now able to transmit data wirelessly to other devices. Measured blood sugar values can, for example, be transmitted from a blood sugar measuring device to a diabetes management apparatus (in particular, a mobile phone) via Bluetooth. In addition, administration apparatuses such as insulin pumps can, for example, transmit the administration history to the same diabetes management apparatus via Bluetooth. Conversely, it is possible to transmit instructions from the data management apparatus to, for example, an administration apparatus. On the one hand, the transmitted data is sensitive data, for example therapy data or measurement data, and, at least in the case of therapy instruction data, the data is patient-critical data that must be protected against unauthorized access. The standard Bluetooth technology already provides various options for making wireless links more secure while they are transmitted. However, the options provided do not cover all conceivable attack scenarios, which is why it makes sense to implement additional security measures (in particular, an additional encryption of the data) at the application level.

Apparatuses and methods are known from WO2017200989 A1 in which one and the same static key are stored on all apparatuses that are to exchange data with one another in order to establish additional security at the application level. This has the disadvantage that the same key is stored on all apparatuses in the system.

In an alternative approach to improving the security of a data exchange link between a glucose monitor (or patch pump) and a control unit, WO2016092448 A1 teaches that a one-time password stored in the glucose monitor (or in the patch pump) can be used to form a key for the Bluetooth link. This means that after a single use, the password is blocked so that no link can be established with another apparatus. The disadvantage of this solution is that a glucose monitor (or a patch pump) always has to be used on the same control unit.

SUMMARY

One object of the disclosure is to provide alternative methods and systems for establishing secure data communication links between portable medical apparatuses and data management devices.

The object is achieved by the method and system according to the disclosure and claims. Further developments and embodiments are set out as well in the description and the drawings.

One aspect of the disclosure is a method for establishing a secure data communication link between a portable medical apparatus, such as an infusion apparatus, an injection apparatus or a blood sugar measuring device, and a data management device. The term "data" is to be interpreted broadly and, in the context of the present document, can include information such as historical data, status information or the settings of the medical apparatus. The term can also include settings, commands and instructions that are transmitted from one apparatus to another. The term "data" can also refer to authentication information or signatures in the context of the communication. The term "medical apparatus" includes (intelligent) apparatuses, which are equipped with the necessary (electronic) processor units, that can be operated by a patient himself/herself and may be worn on the patient, such as for a subcutaneous administration of drugs or for measuring physiological parameters. The apparatuses also include additional (intelligent) apparatuses which can be detachably connected to a mechanical injection apparatus.

In one aspect, the method, according to implementations of the present disclosure, comprises at least the following steps: out-of-band (OOB) transmission of a public key as well as further optional information from the medical apparatus to the data management device. The medical apparatus and the data management device also establish a Bluetooth (BT) link, which is encrypted, regardless of the public key that is transmitted. After this BT link has been established, the data management device transmits a public key to the medical apparatus via the established BT link. The data management device calculates a shared secret (e.g., a piece of data, known only to the parties involved, transmitted in a secure communication; it can be a password, a passphrase, a big number, or an array of randomly chosen bytes) from the public key transmitted from the medical apparatus to the data management device and a secret key from the data management device, and vice versa; the medical apparatus calculates the same shared secret as the data management device from the public key transferred from the data management device to the medical apparatus and a secret key from the medical apparatus. As a result, an encrypted end-to-end link is set up on the basis of the shared secret, deriving a shared key (which can but does not have to match the shared secret) that was calculated by the medical apparatus and the data management device. This end-to-end encrypted link is created in the so-called application security layer (ASL), i.e., on the application level, while the BT link on the transport level also includes an encryption.

Compared to the prior art, the present disclosure has the advantage that, on the one hand, the BT protocol adds additional encryption to the standardized encryption, and on the other hand, a particular medical apparatus can be (consecutively) connected to different data management devices.

In one aspect of the present disclosure, the public key is transmitted from the medical apparatus to the data management device by means of near field communication, such as, NFC. Near field communication has the advantage that it only works between apparatuses if the apparatuses are (geometrically) very close to each other, in the range of centimeters, which makes it difficult to intercept the communication.

In one aspect of the present disclosure, the medical apparatus displays the public key to be transmitted on, for example, a display. In possible embodiments, the key may be generated dynamically and, for example, be displayed on the exemplary display for a certain period of time. To receive the public key from the medical apparatus, the data management device can comprise a suitable optical means, such as a camera, with which the displayed key is recorded. The medical apparatus can display the key as a barcode, a QR code, another graphic representation or as text.

In an alternative aspect of the present disclosure, the public key which is transmitted from the medical apparatus to the data management device can be arranged on the medical apparatus. For this purpose, the key can be printed or adhered onto the housing of the medical apparatus (e.g., in the form of a label), so that it can be received in the data management device via a camera on the data management device. In a further embodiment, the key can be arranged on the packaging of the medical apparatus or on an insert placed in the packaging. The key can be displayed as a barcode, a QR code, another graphic representation or as text.

In one aspect of the present disclosure, the BT link, such as Bluetooth LE, is established according to the Just Works principle as described in the Bluetooth specification Version 5: Bluetooth Core Specification V 5.0, Dec. 6, 2016, which is available at www.bluetooth.com/specifications/archived-specifications and hereby fully incorporated into this document by reference. When establishing the BT link, an action such as a Diffie-Hellman-like key exchange, as made possible according to the BT specification, may take place. In one possible embodiment, the keys are generated using the Elliptic Curve Diffie-Hellman P256 method. The medical apparatus and the data management device exchange public keys on the Bluetooth transport level via the BT link (which is still unencrypted at this point) and, in parallel, generate a shared secret from the public key received from the other apparatus and their own secret key. This shared secret is the basis for a shared long-term key, which serves as the basis for further communication between the two apparatuses. The shared secret can represent the long-term key, or a long-term key will be derived from the shared secret either once, repeatedly or periodically. According to the present disclosure, the long-term key is 128 bits long or longer. An encrypted BT link is thus established between the medical apparatus and the data management device, via which the data management device can transmit its public key and via which the end-to-end encrypted data, according to the present disclosure, is encrypted again.

In one aspect of the present disclosure, long-term keys are also generated for end-to-end encryption (analog), which are validated and, after a successful validation, stored in both apparatuses on the application level.

In one aspect of the present disclosure, the pair of public and secret keys for an end-to-end encryption is generated dynamically in the medical apparatus and/or the data management device. For example, a pair of keys can be newly generated for each new link from a medical apparatus to a data management device in the medical apparatus and/or in the data management device. Alternatively, it is also possible that a pair of keys is generated in a medical apparatus when the medical apparatus is started for the first time, and the pair of keys is not further changed afterwards. In a further alternative, the pair of keys of the medical apparatus is generated in the production plant, such as in the context of the device testing, and is then not further changed. In a further embodiment according to the present disclosure, the pair of keys for an end-to-end encryption is generated in the data management device when the software is installed on the device. Alternatively, for example, a new pair of keys is generated for each new link or renewed regularly (time-dependent).

In one aspect of the present disclosure, the present disclosure relates to a system which consists of at least one medical apparatus and one data management device, between which a secure data transmission link according to the present disclosure may be established. In one embodiment of this aspect, the data management device is a mobile phone, such as a smartphone (such as an Apple iPhone) or a handheld computer (such as a tablet, for example, in the form of an Apple iPad). In a further alternative embodiment, the data management device can also be designed as a dedicated data management and control device for the at least one medical apparatus, such as for a personal diabetes manager (PDM). In a further alternative, the data management device can also be a PC or a PC notebook. In one embodiment of this aspect, the medical apparatus can be designed as an infusion pump, for instance as an insulin pump. A variant of this embodiment can be a conventional insulin pump. In a further variant of this embodiment, the insulin pump can be a so-called patch pump, which is worn directly on the skin. The patch pump may also have a modular structure and consist of at least one disposable module, which includes a reservoir, and a reusable module, which includes at least parts of the control electronics. The conventional insulin pump comprises a display on which the public key of the insulin pump for the end-to-end encryption, according to the present disclosure, may be displayed for the OOB transmission. Alternatively, the public key can also be permanently arranged on the housing. For an OOB transmission, the patch pump can comprise an NFC tag on which the public key, such as a dynamically generated public key, is stored in a readable manner. Alternatively, the public key can also be printed onto the housing of the patch pump. Also with regard to the conventional insulin pump, the OOB transmission of the public key can take place in one variant via NFC as well.

In a further embodiment of this aspect, the medical apparatus can be designed as a blood glucose meter or as a (quasi) continuous blood sugar measuring device. In particular, the same methods described above can be used for the OOB transmission from such a medical apparatus to the data management device.

In a further embodiment of this aspect, the system can comprise several medical apparatuses in the form of infusion and measuring devices, such as at least one insulin pump and one blood glucose meter and, as an alternative or in addition to the blood glucose meter, a (quasi) continuous blood sugar measuring device.

BRIEF DESCRIPTION OF THE DRAWINGS

Implementations according to the disclosure are described below in connection with the attached figures. These are intended to show the basic possibilities of the present disclosure and are in no way intended to be interpreted as restrictive.

FIG. 1 is a symbolic or schematic representation of a smartphone and an infusion pump during the out-of-band key transfer from the pump to the smartphone in a first embodiment. (Phase 1)

FIG. 2 is a symbolic or schematic representation of the first embodiment in the stage in which a BT link is established between the smartphone and the infusion pump according to the Just Works principle. (Phase 2)

FIG. 3 is a symbolic or schematic representation of the first embodiment during the transmission of the public key of the smartphone via the BT Just Works link and the subsequent setup of the end-to-end encryption in the application level. (Phase 3)

FIG. 4 shows how the partial views of FIG. 4A and FIG. 4B together show a sequence diagram for the first embodiment.

FIG. 5 shows how the partial views of FIG. 5A and FIG. 5B together show a sequence diagram for a second embodiment.

DETAILED DESCRIPTION

Figure 4A:
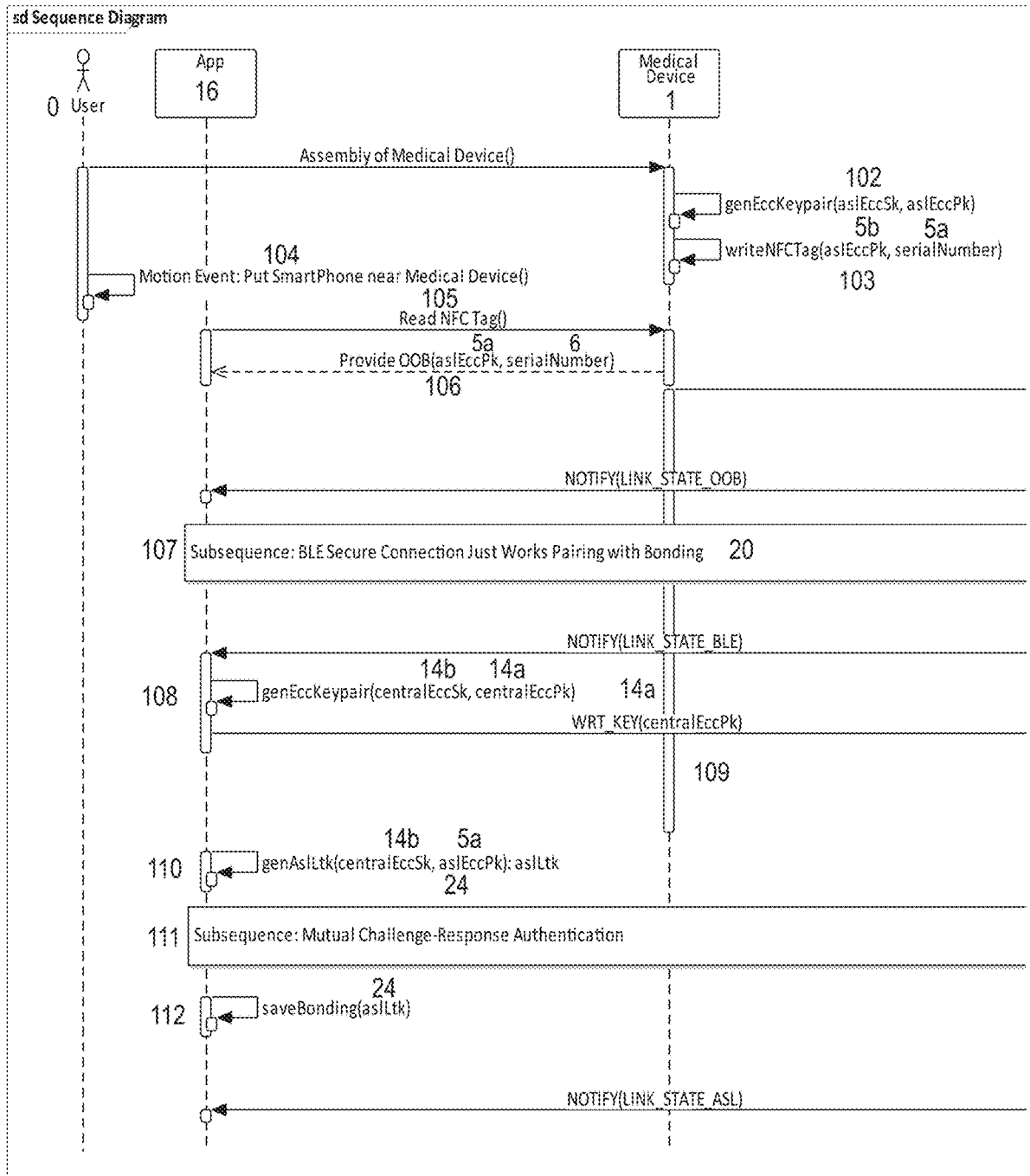
FIG. 4 consists of FIGS. 4A and 4B.
Figure 4B:
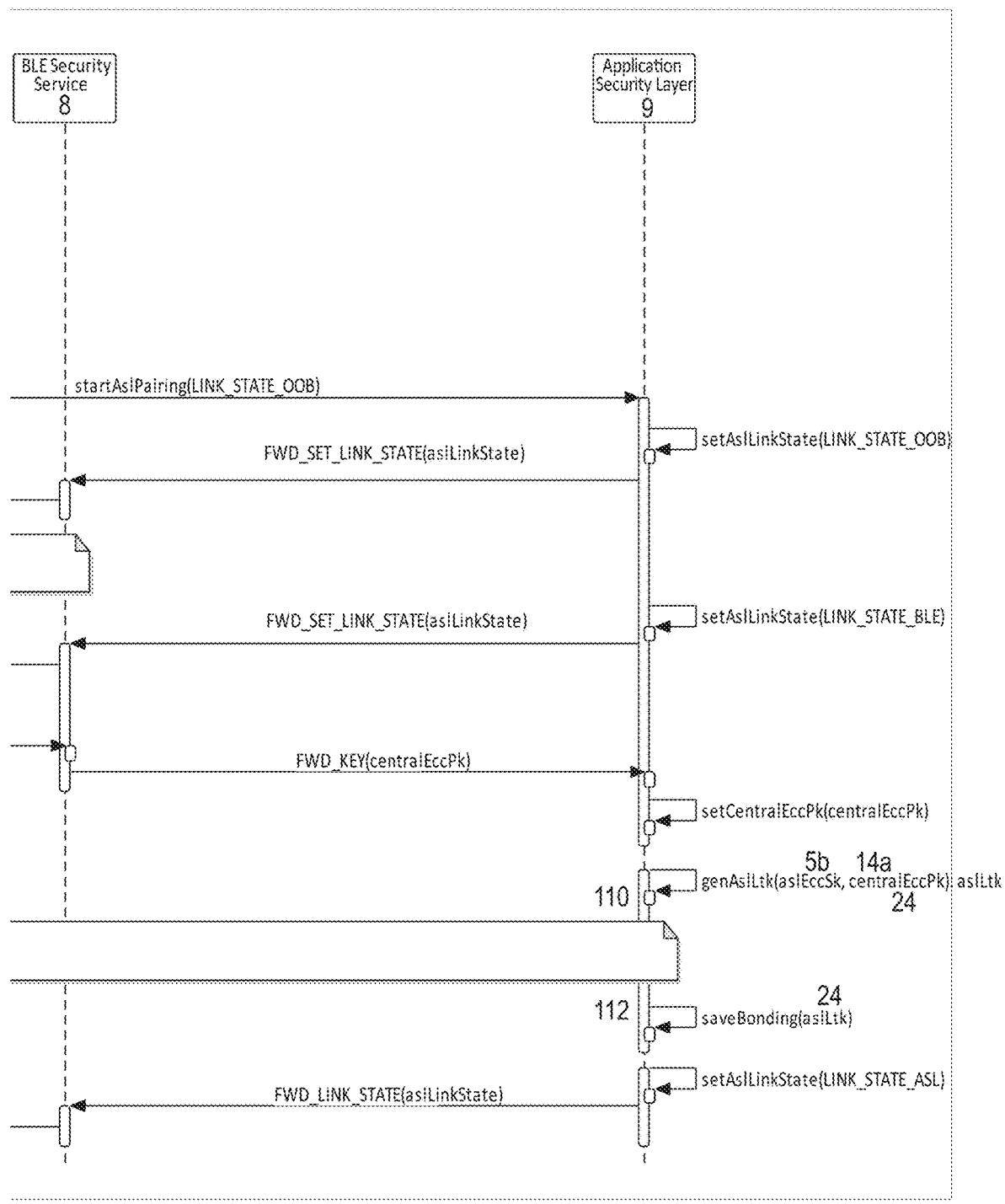

The present disclosure is illustrated below with the help of two examples. These suggest to a person skilled in the art further embodiments, according to the present disclosure, which comprise more apparatuses and devices. These further embodiments are encompassed in the present disclosure. The examples of the present disclosure provided below are kept simple in order to be able to clearly explain the basic concept of the embodiments.

FIGS. 1 to 4A-4B relate to a first embodiment of the present disclosure. In this first embodiment, the system comprises at least one data management device configured as a smartphone 10 and one medical apparatus configured as a modular patch pump for insulin 1. FIGS. 1 to 3 symbolically or schematically show the various phases of the establishment of the secure data communication link. The smartphone 10 can be, for example, a Galaxy S9 from the manufacturer Samsung with all its properties and specifications. A detailed description of the properties and specifications of a smartphone—unless necessary for the presentation of the present disclosure—is dispensed with at this point, since these are prior public knowledge. The patch pump 1, which is conceptually also referred to as a "Pflasterpumpe" in German-speaking countries, is described, for example, in the patent application EP 3443996 A1, with EP 3443996 A1 hereby being fully incorporated into the present document by reference. As mentioned, the patch pump has a modular design and comprises a reservoir unit 2 and a control unit 3, which may be detachably connected to one another. The control unit 3 comprises at least part of the control electronics of the patch pump 1. For instance, the control unit 3 comprises an NFC unit 4 (FIG. 1) for near field communication and a Bluetooth unit 7 (FIG. 2) for setting up and maintaining Bluetooth links with other devices, such as the smartphone 10. The smartphone 10 also includes, in particular, an NFC unit 11 (FIG. 1) and a Bluetooth unit 13 (FIG. 2). The medical apparatus 1 is activated by a near field communication signal of the data management device and switched from a power saving mode or standby mode to an operating mode. The smartphone 10 also includes a display 12 and at least one camera 15. The smartphone also includes an operating system, e.g., Android, as well as an app 16 (both stored in memory), which is used for a data exchange with the medical apparatus 1 and/or the control of the same. In the example of the first embodiment presented here, the patch pump 1 does not have a display.

The method for setting up the secure data communication link, according to the present disclosure, is described below with reference to FIGS. 1 to 4A-4B. The method goes through different phases. Phase 1 is shown in FIG. 1. In this phase, the control electronics of the patch pump 1 are activated and have dynamically generated a pair of keys for the end-to-end encryption to be established. This pair of keys consists of a public key 5a and a secret key 5b. In phase 1, the public key 5a is stored in the NFC unit 4 so that it can be read by external NFC readers, wherein the NFC unit 4 can include a so-called NFC tag for this purpose. In addition, the control electronics of the patch pump 1 also store information 6 on the patch pump, such as a device identification or a serial number, which is also readable in the NFC unit 4. In phase 1, the app 16 is launched on the smartphone and a function programmed and contained therein for setting up a link with a medical apparatus is selected, with the NFC unit 11 and Bluetooth unit 13 of the smartphone 10 being activated. As soon as the app 16 is ready, the smartphone 10 is moved so close to the patch pump 1 that the NFC unit 11 of the smartphone 10 reads the public key 5a and the device information 6 stored in the NFC unit 4 and can transmit them to the app 16; this type of key transfer is called an out-of-band (OOB) transmission 22, because the actual data communication link is subsequently set up via Bluetooth and not NFC.

After the successful transmission of the described data via NFC, the app 16 or the patch pump 1 initiates in phase 2 (see FIG. 2) the setup of a Bluetooth link 20, in particular Bluetooth LE, such as Bluetooth LE Secure Connection, according to the Just Works principle, wherein an encrypted link 20 is established between the Bluetooth units 7 and 13. When setting up the BT link according to the Just Works principle, a Diffie-Hellman or a Diffie-Hellmann-Merkle key exchange may be used in some implementations. After phase 2, an encrypted link therefore exists between the patch pump 1 and the smartphone 10. It is important here that, when using the smartphone 10, the data is only encrypted as far as the Bluetooth unit 13 so that there is the possibility that apps other than the app 16 can access the data as well.

For this reason, among other things, an additional encryption of the data is used according to the present disclosure, which decrypts the data only within the app container of the app 16, so that it is ensured that only the app 16 has access to the transmitted data. This additional encryption is established in phase 3 (see FIG. 3). For this purpose, the app 16 has also generated a pair of keys, which consists of a public and a secret key. The unencrypted public key 14a is now passed on from the app 16 to the Bluetooth unit 13, which sends the key 14a via the (encrypted) Bluetooth link 20 to the patch pump 1, where the Bluetooth unit 7 passes the public key on for further processing. The patch pump 1 now calculates the shared secret 23 from the public key 14a of the app 16 (smartphone 10) and the secret key 5b according to the principle of the Diffie-Hellman or Diffie-Hellman-Merkle key exchange and secret generation. Finally, a symmetrical long-term key 24 is derived from the secret, which is deposited (stored) in the app 16 or the patch pump 1, respectively, for this link. As mentioned above, the shared secret can serve directly as a long-term key, or a long-term key is derived from said secret once, repeatedly or periodically. The long-term key 24 is then used for an end-to-end encryption between the app 16 and the patch pump 1, wherein AES-CCM 128 bit or ChaCha20-Poly1305 can, for example, be used as the encryption method for the end-to-end transmission of the data.

Typically, the correct calculation of the secret and the long-term key 24 is checked by a validation (or authentication) process. The app 16 can, for example, send an encrypted random number to the patch pump 1. The patch pump 1 decrypts the random number and uses said number to carry out a specified mathematical operation and sends the encrypted result back to the app 16. The operation carried out by the patch pump 1 is also stored in the app 16 so that the decrypted result can be checked in the app 16. In addition, the validation process can be repeated by the patch pump 1 or it can basically originate from the patch pump 1. After the potential validation has been successfully completed as well, the end-to-end encrypted transmission of information such as historic data, setting details or commands (the term data should therefore be interpreted broadly) between the app 16 and the patch pump 1 is possible, and an authenticated exchange of end-to-end encrypted data is possible between the app 16 and the patch pump 1. Data packets may also be signed by the sending apparatus.

FIG. 4A&B shows the sequence diagram on which the method is based for phases 1, 2 and phase 3 with validation. The sequence diagram is divided into four columns (from left of FIG. 4A-4B): The user 0, the app 16, the patch pump 1, with a distinction being made between the BT security service 8 and the application security layer 9 (application level) in the patch pump 1. The sequence of operations is described by way of example, the description being simplified and the details from FIG. 4A-4B being understood by a person skilled in the art. The sequence starts when the user 0 assembles the medical apparatus/device, here the patch pump 1 (step 101), whereby the patch pump is activated, which generates the pair of keys 5a, 5b (step 102; as/EccSk, as/EccPk), and writes the generated public key 5a (as/EccPk) and apparatus information 6 (serial-Number) into the NFC unit 4 (step 103). The user 0 now moves the smartphone 10 close to the patch pump 1 (step 104) so that the NFC unit 11 of the smartphone 10 can read the NFC unit 4 (step 105; NFC Tag), with the public key 5a and the device information 6 being transmitted from the patch pump 1 to the smartphone 10 (step 106; as/EccPk). The Bluetooth Just Works link 20 (FIG. 2) is then established in step 107. The smartphone 10 then generates a pair of keys 14a, 14b (centralEccSk, centralEccPk) in step 108 and transmits the public key 14a (centralEccPk) via the BT link 20 to the patch pump 1 in step 109. The long-term key (as/Ltk) 24 is now generated on both devices, the patch pump 1 and the smartphone 10 (in the app 16) (step 110). Now that the common long-term key 24 is known, a validation of the end-to-end encryption 21 can take place via the challenge process 111 (also called the Mutual challenge-response authentication process). If this validation is successful, the sequence is completed by storing the long-term key (as/Ltk) 24 (step 112). This occurs at both ends of the BLE link, as does Bonding (step 112; saveBonding). The linked state is set (As/LinkState) and communicated back to the app 16 via BLE Security Service 8.

In a second embodiment, as in the first embodiment, the system comprises a smartphone 10 as a data management device. In contrast to the first embodiment, the medical apparatus/device is not a patch pump but either a conventional insulin pump or a blood glucose meter (both designated as 30 in FIG. 5A-5B). In this embodiment, the medical apparatus/device 30 has a display in the form of, for example, an LCD or OLED display 31. Text or a graphic representation (for instance, as a QR code or barcode) can be displayed dynamically on the display.

The method, according to the present disclosure, for setting up the secure data communication link between the app 16 and the medical apparatus 30 differs from the first embodiment in phase 1.

In contrast to the first embodiment, the public key 32a (as/EccPk) of the medical apparatus 30 is not transmitted via NFC but instead is displayed on the display 31 in text form or as a graphic representation 33 (for instance, the graphic representation 33 can also contain information about the apparatus 37). The transmission takes place optically in that the at least one camera 15 arranged on the smartphone 10 scans the display 31 of the medical apparatus/device 30, and the app 16 extracts the representation 33 of the public key 32a and apparatus information 37 from the scanned image and then generates the key 32a itself. The key 32a (as/EccPk) is then used further analogously to the first embodiment. Phases 2 and 3 are the same in the second embodiment as in the first embodiment. Reference is made accordingly.

Figure 5A:
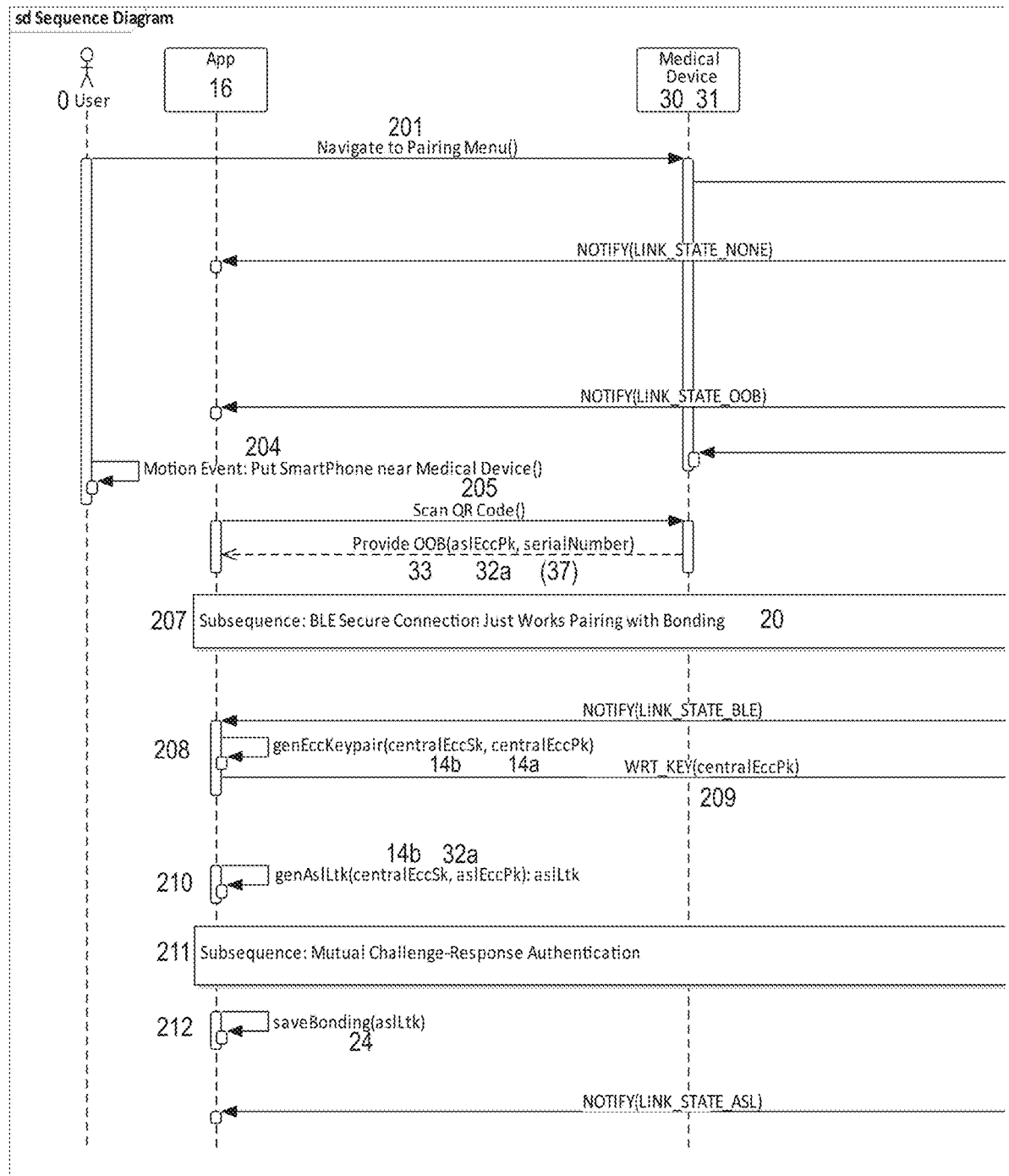
FIG. 5 consists of FIGS. 5A and 5B
Figure 5B:
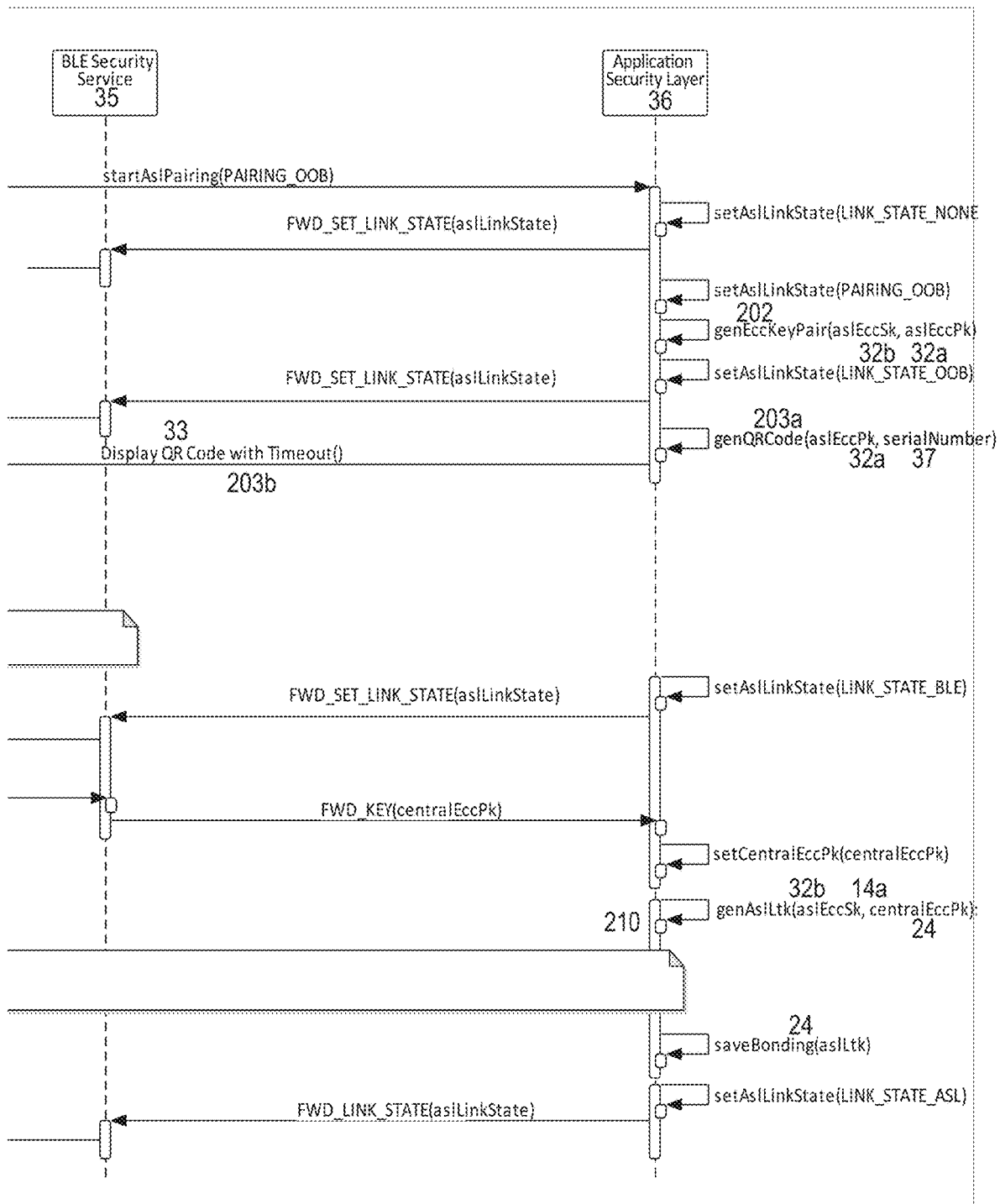

FIG. 5A-5B shows the corresponding sequence diagram for the second embodiment. In step 201, the user 0 navigates to the pairing menu in the menu of the medical apparatus/device 30 in order to start the pairing process. The pair of keys 32a, 32b is then generated in step 202 (as/EccPk, as/EccSk). In the next step 203a, the medical apparatus/device 30 also generates the graphic representation 33 (here a QR code as an example) from the public key 32a and associated device information 37, which is then shown on the display 31 (step 203b). The user 0 moves the smartphone 10 with the camera 15 towards the medical apparatus 30 (step 204) and then scans the graphic representation (e.g., QR code) 33 with the camera 15 (step 205). The further sequence follows analogously to the first embodiment. The BT Just Works link 20 is set up (with Bonding) accordingly in step 207. The pair of keys 14a, 14b (centralEccPk, centralEccSk) is then generated in the smartphone 10 (step 208), and thereafter the public key 14a (centralEccPk) is transmitted to the medical apparatus/device 30 via the BT link 20 (step 209). The medical apparatus/device and the smartphone then generate the long-term key 24 (step 210) and validate said key via the challenge-response authentication process (step 211). Finally, and after the end-to-end encryption has been successfully validated, the long-term key 24 is stored in both apparatuses 10 and 30 in step 212.

LIST OF REFERENCE NUMBERS

0 User
1 Patch pump
2 Reservoir unit
3 Control unit
4 NFC unit
5a Public key
5b Secret key
6 Apparatus information
7 Bluetooth unit (Medical device)
8 Bluetooth security service
9 Application security layer (medical apparatus)
10 Smartphone
11 NFC unit
12 Display (Smartphone)
13 Bluetooth unit (Smartphone)
14a Public key
14b Secret key
15 Camera
16 App
20 Bluetooth Just Works link
21 End-to-end encrypted link via Bluetooth
22 Out-of-band transmission
23 Shared secret
24 Long-term key 30 Medical device/apparatus (e.g., insulin pump or blood glucose meter)
31 Display (Medical device)
32a Public key
32b Secret key
33 Graphical representation of 32a
34 Bluetooth security layer
36 Application security layer
37 Apparatus information
101 Assembly of the patch pump 1
102 Generation of the public 5a and the secret 5b key in the patch pump 1
103 Writing process in the NFC unit 4 for the public key 5a and the apparatus information 6
104 Movement of the smartphone 10 close to the patch pump 1
105 Reading of the NFC unit 4 by the NFC unit 11
106 Transmission of the public key 5a and apparatus information 6
107 Setup of a Bluetooth Just Works link
108 Generation of the public 14a and the secret 14b key in the smartphone 10
109 Transmission of the public key 14a via a Bluetooth link 20
110 Generation of the long-term key 24
111 Challenge process
112 Storage of the long-term key 24
201 Navigation to the pairing menu
202 Generation of the public 32a and the secret 32b key in the medical apparatus 30
203a Generation of the graphic representation 33
203b Display of the graphic representation 33 on the display 31
204 Movement of the smartphone 10 in front of the medical apparatus 30
205 Scanning of the display 31 with the camera 15
207 Setup of a Bluetooth Just Works link
208 Generation of the public 14a and the secret 14b key in the smartphone 10
209 Transmission of public key 14a via a Bluetooth link 20
210 Generation of the long-term key 24
211 Challenge process
212 Storage of the long-term key 24

The invention claimed is:

1. A method for establishing a secure data communication link between a medical apparatus and a data management device, wherein the data management device and the medical apparatus each comprise a Bluetooth unit, and wherein the method comprises the following steps:
   out-of-band transmitting of a public key of a pair of keys from the medical apparatus and of device information from the medical apparatus to the data management device, with the transmitting not taking place via Bluetooth;
   setting up of an established and encrypted Bluetooth data communication link between the medical apparatus and the data management device, wherein the step of setting up of an encrypted Bluetooth data communication link is based on a Just Works principle or use of a Just Works link;
   transmitting of a public key of a pair of keys of the data management device from the data management device to the medical apparatus via the established and encrypted Bluetooth link;
   calculating a combined key on the data management device from the transmitted public key of the medical apparatus and a secret key of the pair of keys of the data management device;
   calculating the same combined key on the medical apparatus from the transmitted public key of the data management device and a secret key of the pair of keys of the medical apparatus; and
   setting up an end-to-end encrypted link between the medical apparatus and the data management device using the combined key with end-to-end encrypted data being transmitted over the established and encrypted Bluetooth link.

2. A method according to claim 1, wherein the out-of-band transmission of the public key takes place by means of near field communication.

3. A method according to claim 1, wherein the out-of-band transmission of the public key takes place by means of a camera of the data management device for optically detecting the public key as displayed by the medical apparatus.

4. A method according to claim 1, wherein the out-of-band transmission of the public key takes place by means of a camera of the data management device, for optically recording the public key arranged on the medical apparatus or on its surface.

5. A method according to claim 1, wherein the public key and the secret key are dynamically generated as a pair of keys by at least one of the medical apparatus and the data management device.

6. A method according to claim 1, wherein the establishment of the Bluetooth link operates according to the Just Works principle and a Diffie-Hellman or a Diffie-Hellmann-Merkle key exchange takes place for the encryption.

7. A method according to claim 6, wherein the Bluetooth link is a Bluetooth LE link, established with the Bluetooth LE Secure Connection Just Works, and in order to exchange keys, and when the Bluetooth LE Secure Connection Just Works is established, an Elliptic-Curve Diffie-Hellman (ECDH) P-256 is used, with a permanent key with a length of 128 bits being determined from the shared key calculated by the ECDH.

8. A method according to claim 1, further comprising validating or authenticating the end-to-end encrypted Bluetooth link after the end-to-end encrypted Bluetooth link has been set up, and storing the combined key in the medical apparatus and the data management device.

9. A method according to claim 2, wherein the medical apparatus is activated by a near field communication signal of the data management device and switched from a power saving mode or standby mode to an operating mode.

10. A method according to claim 9, wherein the pair of keys of the medical apparatus consisting of a public key and a secret key are dynamically generated in the medical apparatus after switching to an operating mode, and wherein this pair of keys is used to set up the end-to-end encrypted Bluetooth link.

11. A method according to claim 3, wherein the medical apparatus comprises a display on which the public key of the medical apparatus and the device information is displayable in the form of a graphic representation so that the graphic representation can be captured by the camera of the data management device, wherein the graphic representation is a barcode, a QR code, an arrangement of alphanumeric characters or another graphic representation.

12. A method according to claim 11, wherein the medical apparatus comprises operating elements which enable a user to force the display of the graphic representation.

13. A method according to claim 11, wherein the public key and the graphic representation are generated dynamically.

14. A method according to claim 1 wherein the medical apparatus is selected from the group comprising: an infusion apparatus, an injection apparatus, or other device for subcutaneous administration of drugs, a blood sugar measuring device, another measuring device for measuring physiological parameters or combinations thereof.

15. A system comprising at least one medical apparatus and a data management device, wherein the data management device has an app installed, in which measured physiological values and/or therapy parameters can be saved, entered and/or processed,
   wherein data can be exchanged between the data management device and the at least one medical apparatus via a wireless Bluetooth link,
   and wherein the Bluetooth link is configured to be securely established with additional end-to-end encryption by the at least one medical apparatus and the data management device communicating to carry out at least the following steps:
   out-of-band transmitting of a public key of a pair of keys from the medical apparatus and of device information from the medical apparatus to the data management device, with the transmitting not taking place via Bluetooth;
   setting up of an established and encrypted Bluetooth data communication link between the medical apparatus and the data management device, wherein the step of setting up of an encrypted Bluetooth data communication link is based on a Just Works principle or use of a Just Works link;
   transmitting of a public key of a pair of keys of the data management device from the data management device to the medical apparatus via the established and encrypted Bluetooth link;
   calculating a combined key on the data management device from the transmitted public key of the medical apparatus and a secret key of the pair of keys of the data management device;
   calculating the same combined key on the medical apparatus from the transmitted public key of the data management device and a secret key of the pair of keys of the medical apparatus; and
   setting up an end-to-end encrypted link between the medical apparatus and the data management device using the combined key with end-to-end encrypted data being transmitted over the established and encrypted Bluetooth link.

16. A system according to claim 15, wherein the system comprises a smartphone, an insulin injection device or an insulin infusion device and a blood glucose meter, and wherein an encrypted link can be established from the smartphone to each of the further devices by means of near field communication.

17. A system according to claim 16, wherein the medical apparatus comprises a continuous or quasi-continuous blood glucose measuring device.

18. A system according to claim 16, wherein links from the smartphone to the additional apparatuses of the system are established by means of near field communication.

19. A system according to claim 15 wherein the medical apparatus is selected from the group comprising: an infusion apparatus, an injection apparatus, or other device for subcutaneous administration of drugs, a blood sugar measuring device or another measuring device for measuring physiological parameters.

* * * * *